Feb. 21, 1961 J. C. MIKKELSEN Plant Pat. 2,029
CHRYSANTHEMUM PLANT
Filed June 2, 1960
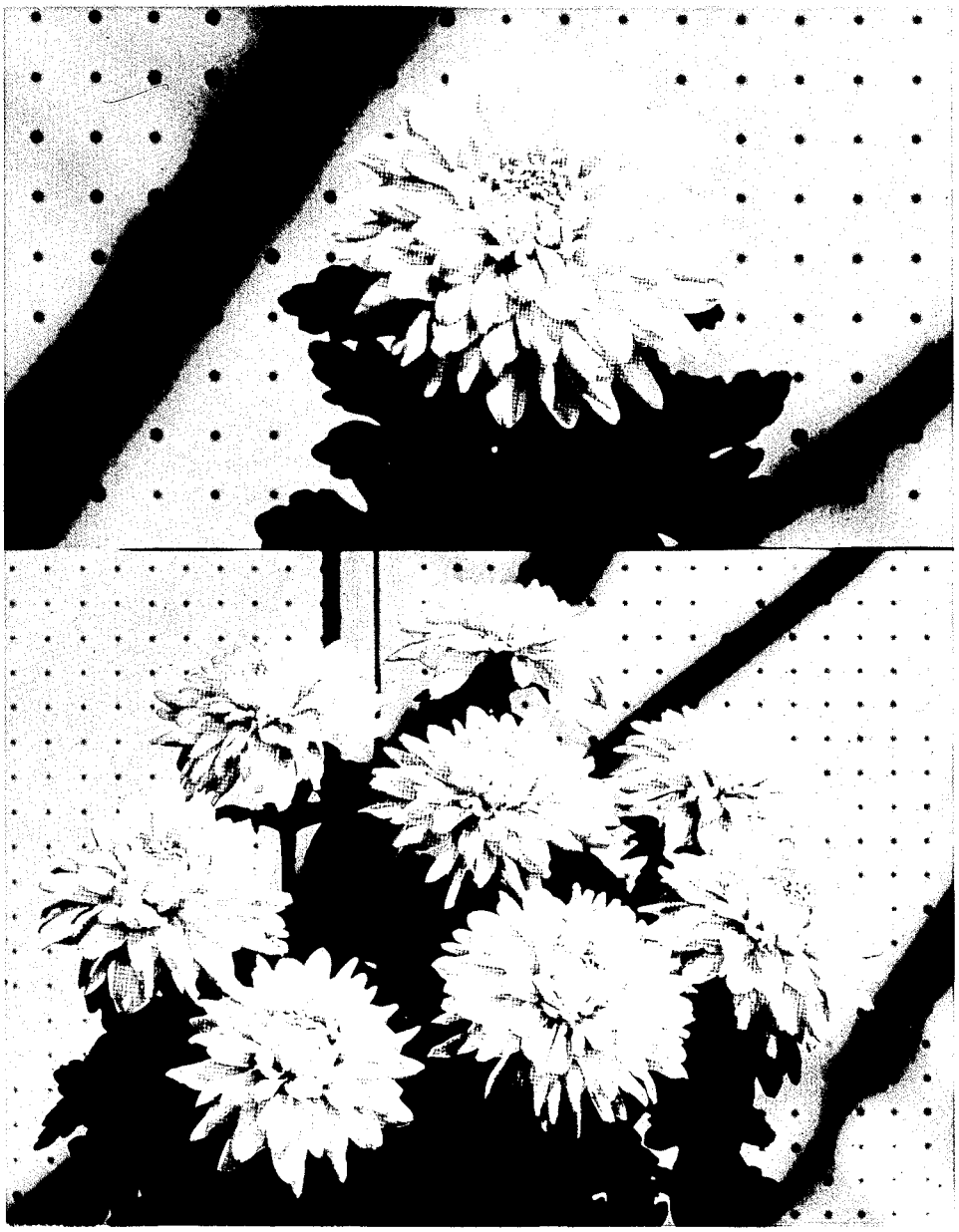
INVENTOR
James C. Mikkelsen
BY Robb & Robb
ATTORNEYS United States Patent Office Plant Pat. 2,029
Patented Feb. 21, 1961

2,029

CHRYSANTHEMUM PLANT

James C. Mikkelsen, Ashtabula, Ohio, assignor to Mikkelsen & Sons Greenhouses, Inc., Ashtabula, Ohio, a corporation of Ohio Filed June 2, 1960, Ser. No. 33,608

1 Claim. (Cl. 47—60)

The present invention relates to a new and distinct variety of chrysanthemum plant of the incurving decorative class, which was discovered by me as a sport of the large-flowering, decorative and incurving variety of chrysanthemum known as "Princess Anne" (unpatented). This parent variety originated in England, and was imported into the United States a number of years ago.

The new sport, which is the subject hereof, was discovered by me amongst potted plants of "Princess Anne" which were being grown under my direction and control in the greenhouses on property owned by my assignee, located at Ashtabula, Ohio. My attention was attracted to one particular potted plant amongst those of "Princess Anne" by virtue of the fact that the plant bore Golden Yellow flowers, contrary to to the normal Peach Pink colored flowers of the variety "Princess Anne." Upon close examination of this plant, I found that it had sported and I thereupon took steps to carefully preserve the sport, keep it under observation, and to later asexually reproduce the same by vegetative cuttings which were propagated by me at Ashtabula, Ohio. These observations and asexual reproductions conclusively established the existence of important differences between the new sport and the parent variety "Princess Anne," and that these differences were fixed and established, and capable of being transmitted through succeeding propagations.

Among the outstanding features of the new variety, the following characteristics contribute to the novelty and distinctiveness thereof, and represent a commercially important and unique combination which is definitely different from that found in the parent variety, or in any other variety of which I am aware:

(1) Lush foliage;

(2) Heavy stems;

(3) A habit of initiating and developing buds at temperatures ranging from 50° to 55° F., which is considerably below the average varieties known in the United States;

(4) Unusual vigor, with attendant ability to grow 12 months of the year;

(5) Large, full flowers, even when grown under adverse conditions of dark winter months in northern latitudes;

(6) A distinctive deep Golden Yellow general color tonality of the flowers;

(7) Good versatility as both a pinched pot plant and as a single stem pot plant; and (8) Suitability for cut flowers when grown under both pinched and single stem culture.

The accompanying drawing shows typical specimens of the flowers and foliage of my new variety, as well as an individual flower specimen on a somewhat larger scale, all as depicted in color as nearly true as it is reasonably possible to make the same in a color illustration of this character.

The following is a detailed description of my new chrysanthemum variety, with color terminology in accordance with Wilson's Horticultural Colour Chart, except where general color terms of ordinary dictionary significance are obvious, as based on specimens grown under pot plant cultural conditions at Ashtabula, Ohio, in the month of January:

Parentage: Sport of "Princess Anne."

Classification: Incurving, decorative.

Growth: Medium height; very upright; heavy broad foliage but not closely spaced; has tendency to produce summer crown buds.

Cold resistance: Not hardy at freezing temperatures, but does initiate and develop its buds at from 50° to 55° F., which is considerably below the average.

Blooming period: From about early November to about mid-or-late November (approximately the 5th to 25th), depending on climatic conditions and day length relative to latitude.

*Flower*

Bud:

*Color.*—When sepals first divide—Lemon Yellow, Plate 4, page 4. When petals begin to unfurl—Buttercup Yellow, Plate 5, page 5. When half-blown; inside of petals—Aureolin, Plate 3, page 3; reverse of petals—Straw Yellow, Plate 604, page 67.

*Peduncle.*—Color—Scheeles Green, Plate 860/2, page 175. Strength—very good; sufficient to hold the flower head even in poor growing seasons.

Bloom:

*Size.*—From 4 to 6 inches, but as high as 7 to 9 inches when ample space is provided.

*Stem.*—Strong; can be grown as pot plant, disbud, or disbudded spray.

*Form.*—Incurving decorative (not a true incurve but rather a flat type).

*Petalage.*—Full (no open center); heavy textured; broad.

*Color.*—Center of flower—Aureolin Yellow, Plate 3, page 3, fading very slightly to outer edges of outside petals to Canary Yellow, Plate 2, page 2. Base of petals—from yellow to green. Inside of petals—Aureolin Yellow, Plate 3, page 3. Reverse of petals—Sulphur Yellow, Plate 1/2, page 1.

*General color tonality.*—Clear and uniform Golden Yellow.

*Petals.*—Texture—heavy. Form—wide, coming to a blunt point on the end.

*Fragrance.*—Flowers have no distinctive fragrance, but leaves have a strong pungent chrysanthemum odor when crushed.

*Plant*

Form: Upright; tends to sometimes throw horizontal breaks after pinching.

Growth: Vigorous; average height.

Foliage: Vigorous; fat; lush; heavy feeder; not prolific in cutting production; arranged alternately and staggered on stems; coarse, without sharp indentations.

*Size.*—Length—from 3 to 5 inches. Width—from 2 to 3 inches.

*Quantity.*—Average.

*Color.*—Upper side—Spinach Green, Plate 960, page 187. Under side—Spinach Green, Plate 960/3, page 187.

*Texture.*—Heavy.

I claim:

A new and distinct variety of chrysanthemum plant of the incurving decorative type, substantially as herein shown and described, characterized particularly as to novelty by the unique combination of lush foliage, heavy stems, a habit of initiating and developing buds well below temperatures of the average chrysanthemum varieties, unusual vigor with attendant ability to grow throughout the year, large and full flowers even when grown under adverse conditions of dark winter months in northern latitudes, a distinctive deep Golden Yellow general color tonality of the flowers, good versatility as both a pinched pot plant and a single stem pot plant, and suitability for cut flowers under both pinched and single stem culture.

No references cited.